United States Patent

Hu et al.

[11] Patent Number: 6,047,040
[45] Date of Patent: Apr. 4, 2000

[54] DETECTOR SIGNAL INTEGRATION IN VOLUMETRIC CT SCANNER DETECTOR ARRAYS

[76] Inventors: Hui Hu, 312 Hillview Cir., Waukesha, Wis. 53188; Armin Horst Pfoh, 16135 W. Maple Ridge Rd., New Berlin, Wis. 53151

[21] Appl. No.: 08/282,671

[22] Filed: Jul. 29, 1994

[51] Int. Cl.⁷ .......................................... A61B 6/00
[52] U.S. Cl. .............................. 378/19; 378/115; 378/116
[58] Field of Search ................................. 378/19, 21, 25, 378/26, 114, 115, 116

[56] References Cited

U.S. PATENT DOCUMENTS

| | | |
|---|---|---|
| 4,160,167 | 7/1979 | Weiss et al. ............................... 378/19 |
| 4,442,489 | 4/1984 | Wagner ....................................... 378/19 |
| 4,965,726 | 10/1990 | Heuscher et al. .......................... 378/19 |
| 5,430,784 | 7/1995 | Ribner et al. ............................. 378/19 |

*Primary Examiner*—David P. Porta
*Assistant Examiner*—Michael J. Schwartz
*Attorney, Agent, or Firm*—Quarles & Brady; Christian G. Cabou; Phyllis Y. Price

[57] ABSTRACT

A multi-slice or volumetric CT system has a 2D array of detector elements arranged in columns along the slice direction and rows along the in-slice direction. Channels in a digital acquisition system connect to the respective columns and a switch assembly is operated during a scan to sequentially enable detector elements in each column either one or two at a time. By enabling two elements at a time, the SNR of the acquired data is increased and the expected resolution loss in the slice direction is compensated for by detector wobbling.

4 Claims, 3 Drawing Sheets

DETECTOR SIGNAL INTEGRATION IN VOLUMETRIC CT SCANNER DETECTOR ARRAYS

BACKGROUND OF THE INVENTION

The present invention relates to computed tomography (CT) imaging apparatus; and more particularly, to the acquisition of data from the separate x-ray detectors in 2D detector arrays.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon a row, or one-dimensional array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

In a volumetric CT system the fan beam also fans out along the z-axis and the detectors are arranged in a 2D array to acquire attenuation measurements in a plurality of slices disposed along the z axis. In some applications, such as lung imaging, high resolution is required in the slice direction and this requires that the dimension along the z-axis of each x-ray detector be very small. Thus, the output signal from each detector can be critically small, particularly in applications where the x-ray beam is highly attenuated. The resulting reduced signal-to-noise ratio can significantly reduce image quality. One aspect of this "low-signal problem" can be solved with more stringent noise requirements on the preamplifiers used in the Data Acquisition System ("DAS") and another aspect can be solved by using more efficient x-ray detector technology. But both of these solutions add considerable expense to the system. The problem can also be solved by increasing the x-ray dose, but this is not a desirable solution considering the increased radiation to the patient.

SUMMARY OF THE INVENTION

The present invention relates to the detector array on a VCT system, and particularly, to the selective combination of detector signals prior to their application to the preamplifiers. More specifically, the VCT system includes a 2D array of detector elements arranged in separate rows disposed along a slice direction and separate columns disposed along an in-slice direction, a set of preamplifiers and associated analog-to-digital converters for receiving and digitizing x-ray attenuation measurements, an image reconstructor for receiving the digitized attenuation measurements and producing a plurality of slice images, and a switch assembly connected to each of the detector elements for controlling the application of x-ray attenuation measurements produced by each of the detector elements to the set of preamplifiers such that x-ray attenuation measurements produced by multiple detector elements located in adjacent rows of the 2D array are applied to one preamplifier.

A general object of the invention is to overcome the low-signal-problems in VCT applications where electronic noise becomes significant relative to quantum statistics noise and is likely to diminish image quality. Under this circumstance, the switch assembly combines the attenuation measurements made by adjacent detector elements to increase the signal level relative to the electronic channel noise. While this may reduce resolution in the slice direction, there are many applications where this is less of a problem than increased noise.

Yet another object of the invention is to increase SNR while minimizing the resolution loss in the slice direction. This is achieved by acquiring one view in which measurements made by one row of detector elements are combined with measurements made by detector elements located in a row to one side, and then acquiring a second view in which measurements are combined with measurements made by detector elements located in a row to the other side. This sampling technique is referred to herein as "detector wobbling" and its use solves the low signal problem without significantly reducing image resolution. When used in combination with focal spot wobbling, detector wobbling provides optimal sampling of the two-dimensional projection data.

DESCRIPTION OF THE PREFERRED EMBODIMENT

Figure 1:
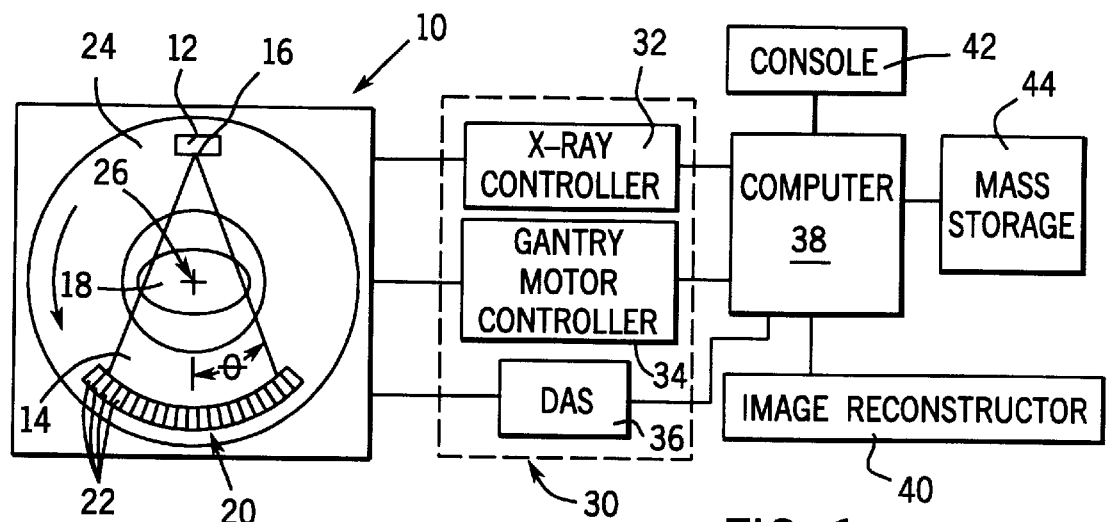
FIG. 1 is a block schematic diagram of the CT imaging system.
Figure 2:
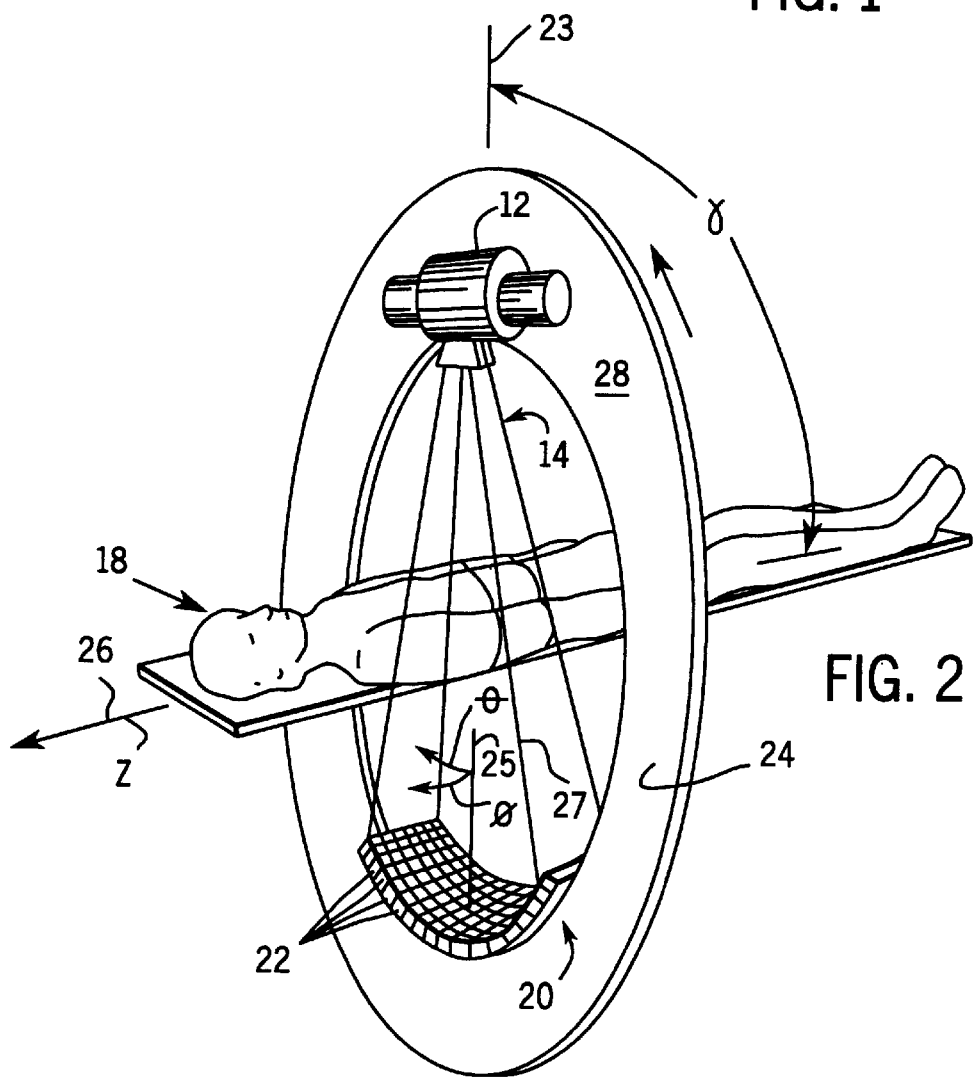
FIG. 2 is a pictorial view of a CT imaging system in which the present invention may be employed.

Referring to FIGS. 1 and 2, a CT system 10 includes an x-ray source 12 oriented to project a cone beam of x-rays 14 from a focal spot 16 through a patient 18 to be received by a two-dimensional detector array 20. The two-dimensional detector array 20 includes a number of detector elements 22 arranged over the area of the detector array 20 in generally perpendicular columns and rows to detect a projected image of the x-rays 14 passing through the patient 18.

The x-ray source 12 and the two-dimensional detector array 20 are mounted on either side of a gantry 24 so as to rotate about an axis of rotation 26 generally positioned within the patient 18. The axis of rotation 26 forms the z-axis of a Cartesian coordinate system having its origin centered within the cone beam 14. The plane defined by the x and y axes of this coordinate system thus defines a plane of rotation, specifically the gantry plane 28 of the gantry 24.

Rotation of the gantry 24 is measured by angle γ from an arbitrary reference position within the gantry plane 28. Angle γ varies between 0 and 2π radians (360°). The x-rays of the cone beam 14 diverge from the gantry plane 28 by angle φ and diverge along the gantry plane 28 by angle θ. The two-dimensional detector array 20 is arranged as a section of the surface of a sphere having a center at the focal spot 16, and its array of detector elements 22 is arranged to receive and make intensity measurements along the rays of the cone beam 14 throughout the angles of φ and θ of the cone beam 14.

Referring to FIG. 1, the control system of the CT scanner 10 has gantry associated control modules 30 which include: x-ray controller 32, which provides power and timing signals to the x-ray source 12, gantry motor controller 34, which controls the rotational speed and position of the gantry 24, and data acquisition system (DAS) 36, which receives projection data from the two-dimensional detector array 20 and converts the data into digital form for later computer processing, while preserving the values of φ, θ and the gantry angle γ at which the data was taken. The x-ray controller 32, the gantry motor controller 34 and the data acquisition system 36 are connected to computer 38.

The computer 38 is a general purpose mini-computer programmed to acquire and manipulate projection data as will be described in detail below. The computer 38 is connected to an image reconstructor 40 which performs high speed image reconstruction according to methods known in the art.

The computer 38 receives commands and scanning parameters via operator console 42 which is generally a CRT display and keyboard that enables an operator to enter parameters for the CT scan and to display the reconstructed image. A mass storage device 44 provides a means for storing operating programs.

Figure 3:
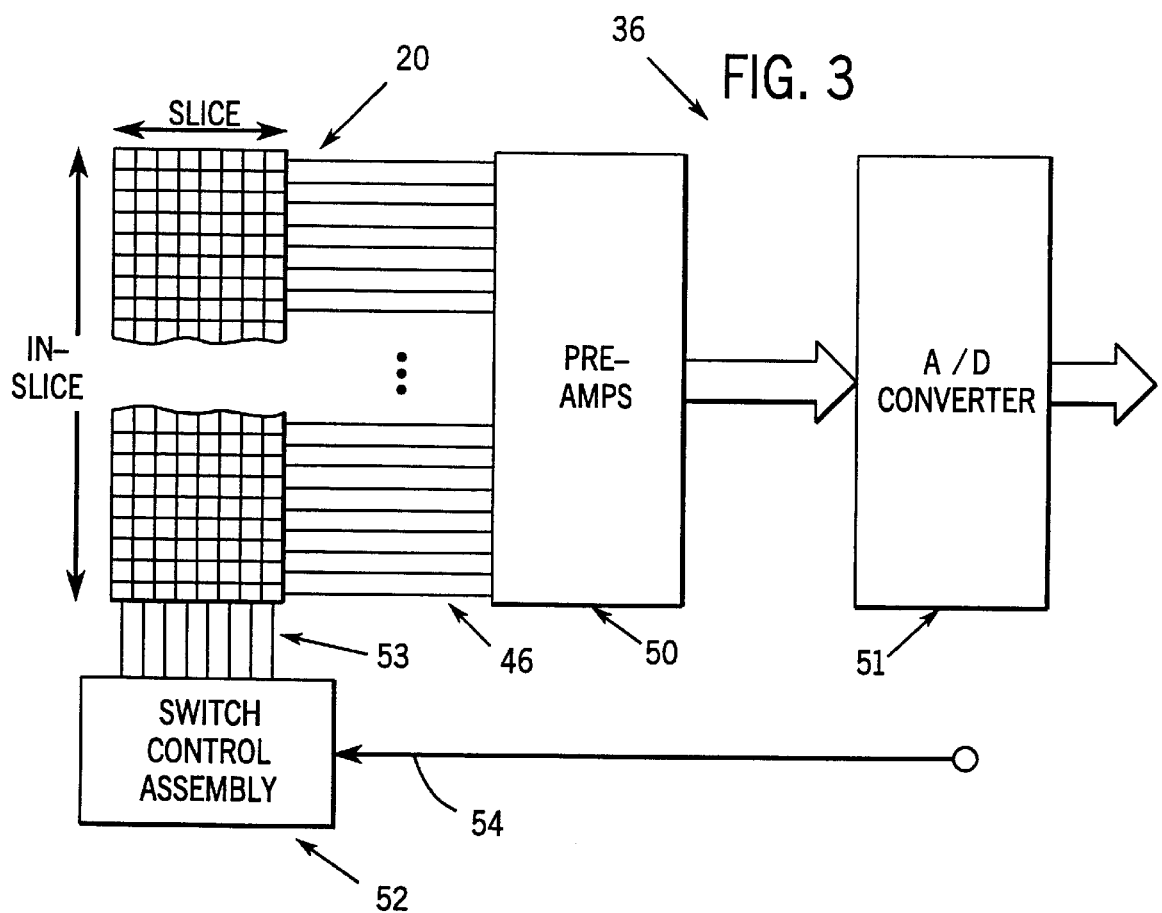
FIG. 3 is an electrical block diagram of the DAS which forms part of the CT imaging system of FIG. 2.

Referring particularly to FIG. 3, the detector array 20 is comprised of a 2D array of detector elements 22 arranged in rows which extend along an in-slice dimension. Each row may include, for example, 1,000 separate detector elements, and the array 20 may include 16 rows disposed along the slice dimension. The detectors 22 may be gas or, solid state detectors which produce an electrical signal proportional to the x-ray flux received over the sample period. For an in-slice resolution of 0.5 mm and a slice resolution of 1.0 mm and a slice at the system isocenter, each detector element 22 may have an area of only 0.5 mm$^2$ at isocenter. As a result, the attenuation measurement signal which they produce is very small, particularly when the x-rays are highly attenuated by the patient. This "photon starved" situation in which electronic noise dominates quantum noise is the major problem addressed by this invention.

Figure 4A:
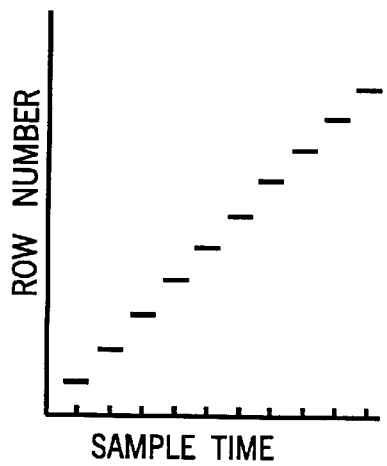
FIGS. 4A and 4B are graphic illustrations of how the DAS of FIG. 3 scans the elements of the detector array.

Referring still to FIG. 3, each detector 22 in a column of the array 20 is connected through an electronic switch (not shown) to an input lead 46 connected to one channel in the DAS 36. Each channel includes a pre-amplifier 50 which receives and amplifies the low-level attenuation measurement, and an analog-to-digital converter 51 which digitizes the amplified measurement. A switch control assembly 52 drives a set of row-enable lines 53 which connect to the electronic switches in corresponding rows of detector elements 22. Signals produced on these row enable lines 53 cause the attenuation measurements made by each row of detector elements 22 to be sequentially applied to the DAS 36. This is illustrated in FIG. 4A where each row of the array 20 is sequentially enabled during successive sample periods and the attenuation measurement made by each detector element 22 in the enabled row is applied to one channel of the DAS 36.

It is a teaching of the present invention that the switch control assembly 52 may be operated by the computer 38 through a control bus 54 to acquire the attenuation measurements from the detector array 20 in a different sequence which enables the attenuation measurements from multiple adjacent detector elements 22 to be combined to boost the signals well above the electronic noise levels of the pre-amplifiers 50.

Figure 4B:
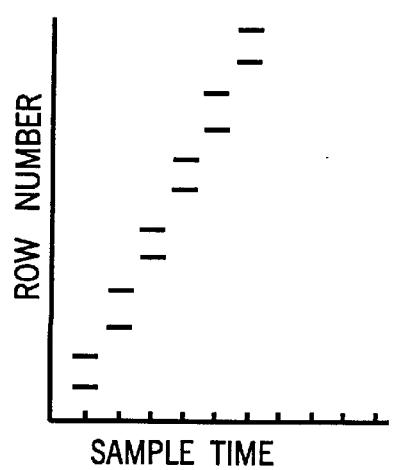

For example, in the first scan sequence illustrated in FIG. 4B, the switch assembly 52 enables a pair of adjacent detector rows during each sample period. Because the measurements are applied to the DAS 36 two at a time, the signal levels are doubled to improve the SNR. Unfortunately, the resolution in the slice dimension is also reduced by one half since this method effectively doubles the size of the detector elements 22 along the slice dimension. Nevertheless, the resolution penalty is well worth the improvement in image quality in those applications where photon starvation is a problem.

In another embodiment of the invention, the photon starvation problem is addressed while minimizing the image resolution loss. This is achieved by acquiring two sets of views. The first set of views is acquired by combining the signal of a detector element in row n with that of the adjacent detector element in row n−1, and the second set of views is acquired by combining the same signal of detector element in row n with that of the adjacent detector element in row n+1. As a result, even though signals are combined to improve SNR, the resolution in the slice direction is not significantly reduced because the distance between samples is only one detector element. This combining of detector element measurements to move the effective location of each sample first to one side and then to the other is referred to herein as "detector wobbling".

Figure 5A:
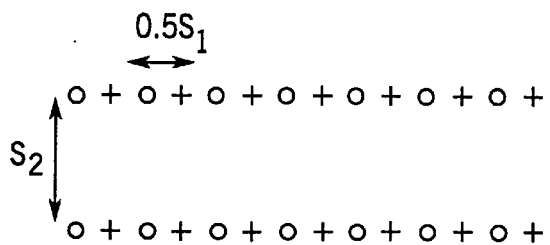
FIGS. 5A and 5B are schematic representations of the sampling pattern that results when focal spot wobbling is employed alone and in combination with detector wobbling as taught by the present invention.
Figure 6:
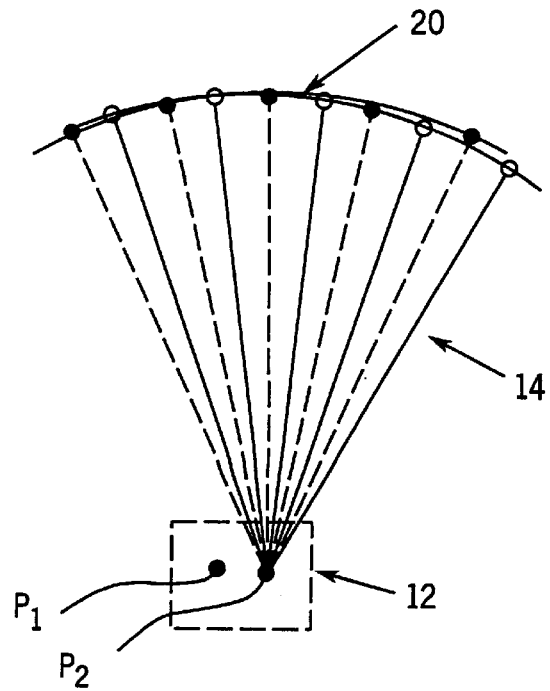
FIG. 6 is a schematic representation of how focal spot wobbling is implemented.

Under normal circumstances, this improvement in SNR without a significant loss of resolution comes at the no expense of scan time. However, when an increase in scan time can be tolerated, a further improvement can be obtained by combining detector wobbling with in-plane focal spot wobbling. As shown in FIG. 6, in-plane focal spot wobbling is achieved by first acquiring a view using a fan beam emanating from one focal spot $P_1$ on the x-ray tube 12, and then acquiring a second view using a second focal spot $P_2$ on the x-ray tube 12. The rotation of the gantry 24 between views is such that the displacement from $P_1$ to $P_2$ cancels the displacement due to the gantry rotation. Thus, the two views are acquired from the same view point and the signals can be combined. This is illustrated in FIG. 5A where the "+" indicate measurements with one focal spot and the "0" indicate measurements with the other focal spot. The in-slice spacing, or "pitch" of the detector elements 22 is $S_1$ and the in-plane spot wobbling effectively cuts this in half. The distance $S_2$ is the pitch in the slice direction when signals from two adjacent detector elements 22 are combined as described above. For a more detailed description of how in-plane spot wobbling is implemented, reference is made to U.S. Pat. No. 5,173,852, entitled "Computed Tomography System With Translatable Focal Spot", which was filed on Jun. 20, 1990 and is incorporated herein by reference.

Figure 5B:
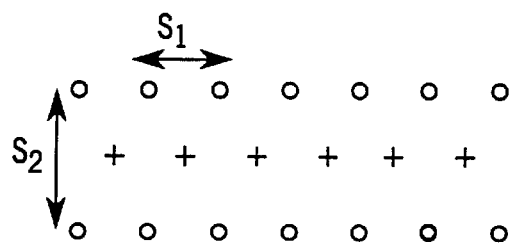

When detector wobbling is combined with in-slice spot wobbling the system effectively doubles the sampling frequencies in both the slice direction and in-slice direction. Also, as shown in FIG. 5B, such "diagonal wobbling" provides the most uniform way to sample a 2D projection. By operating the switch assembly 52 under the direction of the computer 38, therefore, the signal strength and detector resolution can be controlled to meet the particular requirements for each scan.

We claim:

1. A computed tomography imaging system which comprises:

a two-dimensional array of detector elements for receiving photons emanating from an x-ray source and producing electrical signals proportional thereto, the detector elements being located in rows which define an in-slice direction and the same detector elements being located in columns which define a slice direction;

a digital acquisition system having a set of pre-amplifiers, one pre-amplifier for each column of the array of detector elements, and each pre amplifier being connected to receive the electrical signals produced by the detector elements in the pre-amplifier's corresponding column of the two-dimensional array of detector elements;

a switch assembly connected to the two-dimensional array of detector elements through row enable lines and being operable in response to control signals to selectively enable the detector elements in each row to apply their electrical signals to their corresponding pre-amplifiers; and computer means for operating the computed tomography imaging system to perform a scan comprised of a series of views in which the switch assembly is operated to enable successive pairs of rows of detector elements such that the electrical signals from successive pairs of detector elements in each column are simultaneously applied to the column's corresponding pre-amplifier.

2. The computed tomography imaging system as recited in claim 1 in which the detector elements in each column are enabled two at a time to produce detector wobbling along the slice direction for each acquired view.

3. A computed tomography imaging system which comprises:

a two-dimensional array of detector elements for receiving photons emanating from an x-ray source and producing electrical signals proportional thereto, the detector elements being located in rows which define an in-slice direction and the same detector elements being located in columns which define a slice direction;

a digital acquisition system having a set of pre-amplifiers, one pre-amplifier for each column of the array of detector elements, and each pre amplifier being connected to receive the electrical signals produced by the detector elements in the pre-amplifier's corresponding column of the two-dimensional array of detector elements;

a switch assembly connected to the two-dimensional array of detector elements through row enable lines and being operable in response to control signals to selectively enable the detector elements in each row to apply their electrical signals to their corresponding pre-amplifiers; and computer means for operating the computed tomography imaging system to perform a scan comprised of a series of views in which the switch assembly is operated to enable successive pairs of rows of detector elements such that the electrical signals from successive pairs of detector elements in each column are simultaneously applied to the column's corresponding pre-amplifier;

in which the detector elements in each column are enabled two at a time to produce detector wobbling along the slice direction for each acquired view in which the x-ray source has two focal spots ($P_1$, $P_2$) from which photons may emanate, and the computer means operates the x-ray source during the scan to produce in-slice wobbling by acquiring successive views with photons emanating from alternate ones of the two focal spots ($P_1$, $P_2$).

4. The computed tomography imaging system as recited in claim 2 in which the detector elements in each column are enabled consecutively first with the detector elements of a previous row, if any, and then with the detector elements of a subsequent row, if any.

* * * * *